United States Patent [19]

Raczka

[11] 4,271,605
[45] Jun. 9, 1981

[54] FLEXIBLE FOOT SUPPORT

[75] Inventor: Edward Raczka, Aurora, Colo.

[73] Assignee: Sea Gull, Denver, Colo.

[21] Appl. No.: 57,606

[22] Filed: Jul. 16, 1979

[51] Int. Cl.³ .............. A43B 13/18; A43B 1/10; A43B 5/00; A61F 5/00

[52] U.S. Cl. .................. 36/28; 36/7.2; 36/7.5; 36/114; 128/80 R; 128/581

[58] Field of Search ............ 36/28, 7.2, 7.4, 7.5, 36/10, 11.5, 114, 131, 132; 128/80 D, 80 R, 595, 621, 622, 581

[56] References Cited

U.S. PATENT DOCUMENTS

| | | | |
|---|---|---|---|
| 2,207,091 | 7/1940 | Fetterling et al. | 36/7.5 |
| 2,454,836 | 11/1948 | Rayner | 128/80 D |
| 2,708,930 | 5/1955 | Lowman | 128/80 D |
| 3,012,343 | 12/1961 | Dinkel | 36/7.2 |
| 3,086,520 | 4/1963 | Scholl | 128/80 D |
| 3,487,830 | 1/1970 | Pruett | 36/7.2 X |
| 3,683,519 | 8/1972 | Creamer | 36/11.5 |

FOREIGN PATENT DOCUMENTS

| | | | |
|---|---|---|---|
| 195640 | 5/1938 | Switzerland | 36/7.5 |
| 327908 | 3/1958 | Switzerland | 128/80 D |

Primary Examiner—James Kee Chi
Attorney, Agent, or Firm—Young & Martin

[57] ABSTRACT

A flexible foot wrap is provided for supporting the metatarsal arch region of the foot and is adapted for use during activities requiring foot covering. The foot wrap has a fabric panel that supports a cushion, and a strap that extends around the heel of the foot and is attached at opposite sides of the panel. A second strap extends over the top midportion of the foot to hold the cushion against the sole of the foot, and this second strap has opposite ends connected to opposite sides of the panel. Preferably the fabric panel and straps are formed of elastic material, and at least one of the straps is formed in two sections that are releasably attachable to one another for purposes of adjustment of the foot wrap to feet of different sizes.

11 Claims, 8 Drawing Figures

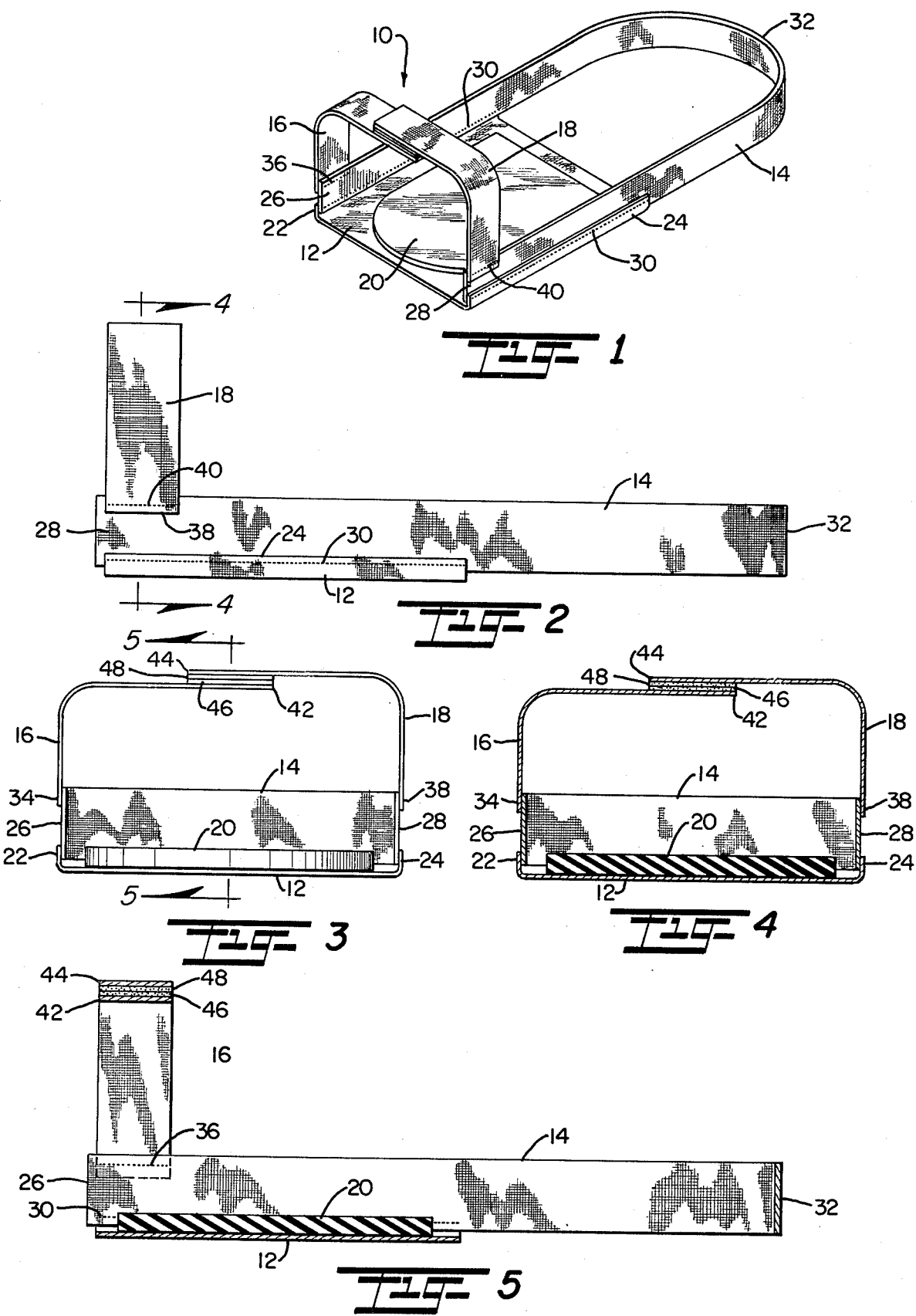

1

FLEXIBLE FOOT SUPPORT

BACKGROUND OF THE INVENTION

The present invention relates to new and useful improvements in flexible foot supports or foot wraps which support the foot of a wearer so as to provide greater comfort as well as protection against certain disruptive forces to which the foot is subjected. More particularly, the present invention is adapted for use by athletes and the like wherein the feet of the athlete are subject to unusual strains as a result of strenuous activities, and particularly provides a useful, self-contained, flexible, elastic appliance or attachment for cushioning, supporting and structurally controlling the foot, thus limiting or preventing secondary compensatory positional deformities in the foot and related physical structure. In the human foot, the longitudinal arch is formed by the seven tarsal bones and the five metatarsal bones and ligaments binding them together. The greatest part of the tensile stress on the longitudinal arch is borne by the lower ligaments. In addition to the longitudinal arch, the foot presents a series of transverse arches at the posterior part of the metatarsals and the anterior part of the tarsus. The transverse arches are strengthened by various ligaments and muscles, and by the tendons which stretch across the arches. The medial longitudinal arch is considerably higher and more important for its function in balance and agility, but, due to its position is more susceptible to damage from strenuous activity. Undesired relaxation of this arch may result from a localized weakness in the arch area and, under strenuous exertion, this weakness can create complex foot problems and create discomfort to the individual. Indeed, strenuous activity itself can often cause a relaxation of the arch which in turn can create pain. In addition, undesirable malformation or displacement of an arch may result from weakness or atrophy of intrinsic muscles associated with the arch.

While the above-noted problems have been recognized in the past, and certain attempts have been made to alleviate the problems, an acceptable foot support or wrap has not been available which may conveniently be worn in an athletic shoe and which effectively supports the athlete's foot properly without migrating during rigorous activities.

An example of a previous attempt to provide a foot pad for the human foot may be found in U.S. Pat. No. 2,454,836 to Rayner, issued Nov. 30, 1948. In this apparatus, a fabric sleeve is positioned underneath a foot by means of two elastic straps extending over the foot at the metatarsal region thereof. The fabric sleeve may receive a support cushion which generally underlies the metatarsal arch of the foot. Other examples of cushioning devices utilized on the human foot may be found in U.S. Pat. No. 2,771,691 to Luchs, issued Nov. 27, 1956, and in U.S. Pat. No. 3,253,601 to Scholl, issued May 31, 1966. Other applications of foot supports for strictly medical purposes may be found in U.S. Pat. No. 3,093,130 to Cotton, issued June 11, 1963, and U.S. Pat. No. 3,861,399 to Huff issued Jan. 21, 1975. This latter device discloses a heel protector and cross-strap assembly within which a heel cushion may be placed and strapped onto the foot inside a shoe.

Both flexible and semi-rigid fabricated foot appliances according to the prior art have unfortunately been often bulky, thereby changing the size of one shoe and thus, ultimately compromising purposeful support and function available to the foot and ankle by that shoe. Another ill or undesirable effect of the shoe inserted flexible or semi-rigid fabricated foot support is the increased weight of the foot and shoe, as well as frictional shear and a decreased tactile sensation in the foot, as it rests upon the appliance within the shoe. As the foot, ankle and knee function during normal activities, ideal foot-shoe fit is essential. A light, non-bulky type of footgear, encompassing appropriate structural foot control is essential in protecting and preventing secondary structural stresses placed on the foot.

The present invention is constructed to eliminate the problems described above, especially when used by athletes and the like, and will function as a soft, but firm device which conforms to the particular morphology of the foot. It solves both the problem of bulk when a foot support is worn inside of a shoe, while at the same time avoids the mislocation of the arch support under the influence of strenuous activity. The present invention, therefore, provides a safe, comfortable support which may be worn during all types of activities.

SUMMARY OF THE INVENTION

It is an object of the present invention to provide a novel foot support apparatus attachable directly to the foot which effectively supports the metatarsal arches of the human foot.

It is a further object of the present invention to provide a comfortable, inexpensive lightweight foot support wrap that is flexible while giving firm support to the foot and which may be releasably secured to the user's foot and which may be comfortably worn inside of various shoes or foot coverings without sacrificing tactile sensation of the foot.

It is yet another object of the present invention to provide a foot support wrap in the form of a support cushion which is positionable to underlie the metatarsal arch region of the human foot and which cushion may be secured against movement therefrom while at the same time allowing virtually unrestrained movement of the various foot joints.

A still further object of the present invention is to provide a foot support apparatus which may be releasably secured to the human foot and which both supports the metatarsal arch under strenuous activities and which limits sagittal plane motion of the heel.

Another object of the present invention is to support the foot in such a manner as to aid in aligning the foot, ankle and knee joints so as to serve as a mode of shock absorption for the foot and lower leg to protect the foot against strains occurring in these joints during rigorous activities.

In the preferred embodiment, the present invention comprises a base support in the form of a fabric panel upon which is mounted a cushion. The panel is preferably of rectangular shape, but can be formed in a variety of configurations suitable to underlie the foot and to mount the cushion in a supported manner against the sole of the foot at a position forward of the heel. The panel and cushion assembly are attached to straps which position the panel and cushion beneath the metatarsal arch of the foot immediately in front of the heel, as described, and a first one of these straps is formed as a loop which extends around the back of the foot at the heel and is attached at its opposite ends to opposite sides of the panel. A second strap is attached to the end portions of the first strap and extends across the top of the foot in a metatarsal region in front of the ankle. Preferably, this second strap is formed as two sections which may be releasably secured together by means of a Velcro strip so that, by placing the first strap and the rectangular panel in position, the Velcro strip provides some degree of adjustment whereby the tightening of the second strap locks the padded cushion into position. This particular mounting provides an improved support by positioning a mass of padding immediately forward of the heel while, at the same time, pressuring the heel against the pad to limit the motion of the sagittal plane of the heel.

Other features increase the effectiveness of the preferred form of the foot wrap. One such feature is the formation of the panel out of an elastic material. Also, the first and second straps may be formed out of elastic material so that the elasticity helps in positioning the padded cushion. In addition, by forming these parts of the invention out of elastic materials, flexibility is provided so that the foot wrap will readily conform to the shape of the foot during its motion which is especially desirable during strenuous activities. Additionally, the use of flexible materials provides a thin, lightweight construction so that the foot support may be worn inside of a foot covering or athletic shoe during strenuous activities without fear of disrupting those activities with wearer discomfort or otherwise, with the elasticity restraining displacement of the cushion.

Other objects, advantages and features of the present invention will become more readily appreciated and understood when taken together with the following detailed description in conjunction with the accompanying drawings, in which:

BRIEF DESCRIPTION OF THE DRAWINGS

FIG. 1 is a perspective view of the preferred embodiment of the self-contained flexible foot wrap according to the present invention;

FIG. 2 is a side view in elevation of the apparatus shown in FIG. 1;

FIG. 3 is a front elevational view of the preferred embodiment of the present invention;

FIG. 4 is a view in cross-section taken about lines 4—4 of FIG. 2;

FIG. 5 is a cross-sectional view taken about lines 5—5 of FIG. 3;

DETAILED DESCRIPTION OF THE PREFERRED EMBODIMENT

Figure 7:
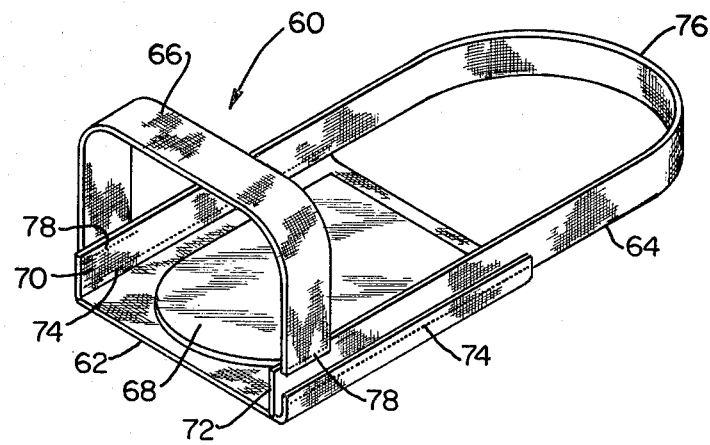
FIG. 7 is a perspective view of an alternative embodiment of the present invention.

The preferred embodiment of the present invention is a self-contained flexible foot wrap which is releasably attachable to the human foot and which may be conveniently and comfortably worn inside of a shoe or other foot covering. The flexible foot wrap is adapted to support the metatarsal arch of the human foot during all times of ambulatory activities, especially during of vigorous activity. Generally, this device may consist of any elastic, linen, rayon or cotton elastic strapping to effect the intended purposes. The body of the invention should consist of a relatively resilient but flexible material to allow arch support and to promote conformation to the contour of the arch within the shoe.

As is shown in FIG. 1, self-contained flexible foot wrap 10 according to the present invention includes a thin, relatively flat or planar base support 12, which, in the preferred embodiment, is a generally rectangular fabric panel, to which is connected an elongated looped strap 14 and a pair of connecting straps 16 and 18. Base support 12 mounts a pad or cushion 20 which is adapted to underlie the metatarsal arch of the human foot when the foot wrap is placed thereon. It should be appreciated that the actual shape of base support 12 may be varied, and indeed the construction thereof altered without departing from the scope of the invention. It is important, however, that base support 12 be suitable to position and retain pad or cushion 20 against the metatarsal arch region immediately forward of the heel H.

As may be seen with more particularity in FIGS. 2-5, base support 12 has opposite sides or edges 22 and 24 which are sewn to opposite end portions 26 and 28 of elongated strap 14, with end portions 26 and 28 being attached entirely along the length of edges 22 and 24. While the attachment of base support 12 to strap 14, in the preferred embodiment, is accomplished by means of stitching 30, it is to be understood that other attachment means would be possible as is known in the art, and it is even possible that base support 12 and strap 14 be formed integrally. In this manner, then, the strap 14 is generally in the form of a loop having a medial portion 32 adapted to extend around the back or heel of the person's foot during use, with the direction of extension laying in a plane generally parallel with the plane of the sole S of the foot.

Similarly, strap 16 has one end 34 attached to end portion 26 of strap 14 by means of stitching 36, and strap 18 has an end 38 attached to end portion 28 of strap 14 by means of stitching 40. Straps 16 and 18 have free ends 42 and 44, respectively, with free ends 42 and 44 adapted to extend around the upper portion of the foot in the metatarsal region thereof and to slightly overlap one another. Free ends 42 and 44 are adapted to be releasably secured to one another, and , in the preferred embodiment, this releasable attachment is accomplished by means of a pair of mating Velcro strips. As is well known, Velcro strips are formed as a mating pair with one of the pair consisting of a matrix of small plastic, hook-like fingers with the other of the pair consisting of a matrix of small loops. When pressed together, the strips adhere to one another although they may be released from one another by forcibly pulling them apart. In the preferred embodiment, free end 46 of strap 16 has a Velcro strip 46 and free end 44 of strap 18 has attached thereto a mating Velcro strip 48. It should be noted that Velcro strips 46 and 48 are attached on facing surfaces of straps 16 and 18 in any suitable manner, and that they will adhere to one another when pressed together.

While the preferred embodiment utilizes Velcro strips as the releasable attachment means for straps 16 and 18, it should be recognized that other suitable attachment mechanisms, such as, hooks and eyes, snaps, or the like, are acceptable. It is only important that the releasable attachment means be of small size so as not to be too bulky or uncomfortable when the flexible foot wrap is worn inside of a shoe. An additional advantage accrues from the use of Velcro strips, however, in that a degree of adjustability is possible since the Velcro strips will adhere along any portion of their length.

In addition to base support 12 and straps 14, 16 and 18, the flexible foot wrap according to the preferred embodiment of the present invention includes a pad or cushion 20. Cushion 20 is attached to base support 12 so that it lies between end portions 26 and 28 of strap 14. Cushion 20 is generally oval in shape and may be attached to base support 12 in any convenient manner such as by an adhesive or by stitching and the like. Cushion 20 should be securely attached to panel 12, however, and best results are achieved when the entire peripheral edge of cushion 20 is affixed to panel 12. By so attaching cushion 20, any tendency for it to tear away from panel 12 is minimized and any tendency for bunching whereby cushion 20 would become doubled or folded together is also minimized. As noted above, when flexible foot wrap 10 is placed on the user's foot, cushion 20 underlies and supports the metatarsal arch of the foot and is positioned immediately in front of the heel and extends substantially the length of the metatarsal arch.

In constructing the flexible foot wrap according to the present invention, a variety of materials may be utilized. It has been found, however, that some materials perform in a superior manner. Although it is important that the material chosen for panel 12 and straps 14, 16 and 18 be flexible so as to conform to the shape of the human foot, the use of a releasable attachment in the form of Velcro strips and the like on straps 16 and 18 permit the utilization of inelastic materials. In the preferred embodiment, however, straps 14, 16 and 18 are a cotton elastic material, and, although cushion 20 may be composed of a gauze-like material, stiff foam, sponge rubber, thermal plastic foam or other type of padding, it is preferably a closed-cell synthetic rubber approximately 0.5 centimeters thick. Of course, cushion 20 may be contoured to have varying thickness should an abnormality in the foot of the wearer require such prescription.

Figure 6:
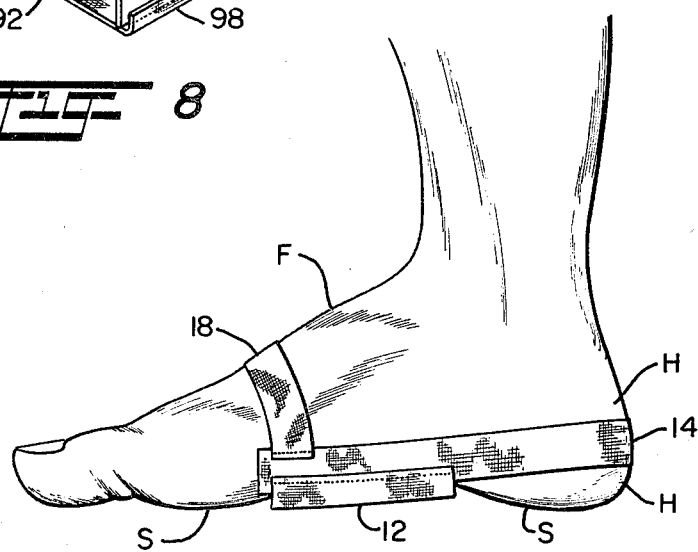
FIG. 6 is a perspective view of the preferred embodiment of the present invention shown attached to a human foot.

To use the flexible foot wrap according to the present invention, as is shown in FIG. 6, the wearer detaches strips 16 and 18 from one another and then places the heel of his foot F between medial portion 32 of strap 14 and panel 12 so that a cushion 20 confronts the transverse arch of the foot along the sole s thereof. The wearer than fastens free ends 42 and 44 of straps 16 and 18 together by means of the Velcro strip, applying the desired force to tighten straps 16 and 18 as well as panel 12 around the metatarsal region of the foot. This firmly secures foot wrap 10 on the foot with the metatarsal arch being supported by a cushion 20. Since the foot wrap is flexible and because of its elastic properties, the foot is free to move through all normal degrees of motion without fear of dislodging the flexible foot wrap. In addition, when used in the described manner, the positioning of straps 14, 16 and 18 in combination with cushion 20 cause the motion of the sagittal plane of the heel to be limited, especially when strap 14 is fairly tight due to the positioning of the foot wrap and the adjustability of straps 16 and 18. Further, the device as attached may be worn inside a sock and shoe or other foot covering without adding too much bulk to the foot. Therefore, a convenient and comfortable support is provided.

ALTERNATE EMBODIMENTS OF THE PRESENT INVENTION

A first alternate embodiment of the preferred embodiment of the present invention is shown in FIG. 7. Here, the Velcro strips 46 and 48 are eliminated from the preferred embodiment with the attachment of the foot support being maintained by the elastic properties of the materials constructing it. As shown in FIG. 7, flexible foot wrap 60 is constructed of a generally rectangular panel 62, an elongated strap 64 and a second elongated strap 66. Panel 62 mounts a pad or cushion 68 which is adapted to unlerlie the metatarsal arch of the human foot when the foot wrap is placed thereon. Panel 62 has opposite sides attached to opposite end portions 70 and 72 of strap 64 by means of stitching 74. In this manner, then, strap 64 is generally in the form of a loop having a medial portion 76 adapted to extend around the back or heel of the person's foot during use.

Similarly, strap 66 has one end attached to end portion 70 of panel 62 by means of stitching 78 with the other end of strap 66 being attached to end portion 72 of strap 64, also by stitching 78.

As should be appreciated, the alternate embodiment shown in FIG. 7 replaces straps 16 and 18 of the preferred embodiment with a single strap 66 so as to omit the releasable attachment or Velcro strip which interconnected straps 16 and 18 in the preferred embodiment. While it is not essential that panel 62 and straps 64 and 66 be formed of an elastic material, performance of the apparatus as well as comfort to the wearer is enhanced if all three pieces are made of an elastic material. In addition, by forming these parts of elastic materials, an additional advantage is gained since one basic size of foot wrap will fit a variety of sizes of feet. When flexible foot wrap 60 is worn, then, it is necessary that the toe of the foot be first inserted between strap 66 and panel 62 after which heel portion 76 may be positioned around the heel of the foot.

Figure 8:
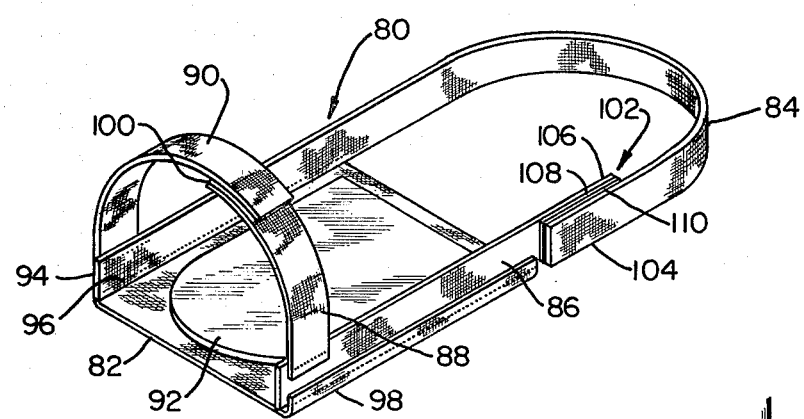
FIG. 8 is a perspective view of a second alternate embodiment of the present invention.

The second alternate embodiment, shown in FIG. 8, modifies the preferred embodiment by adding means for a second releasable attachment. Broadly, the second alternate embodiment of foot wrap 80 has a bottom panel 82 to which is attached a pair of straps 84 and 86 and a second pair of straps 88 and 90. Panel 82 supports a cushion or pad 92 which is secured to one surface thereof, and is further attached to end 94 of strap 84 by means of stitching 96. Similarly, the opposite side of panel 82 is attached to strap 86 by means of stitching 98. Straps 88 and 90 are attached to straps 84 and 86 in an identical manner as that described with respect to straps 16 and 18 of the preferred embodiment. Further, straps 88 and 90 support a Velcro connector 100 as described with respect to the preferred embodiment.

The point of departure of the second alternate embodiment as shown in FIG. 8 and the preferred embodiment resides in the addition of a second Velcro connector 102 which is provided to interconnect ends 104 and 106 of straps 84 and 86, respectively. Velcro connector 102 comprises a pair of mating Velcro strips 108 and 110 with one member of the pair each being secured to ends 104 and 106 of straps 84 and 86 so that they may be releasably attached to one another. Again, the function of the releasable Velcro connector 102 has been described with respect to Velcro strips 46 and 48 so that it need not be described again. It should be appreciated, however, that, with the addition of Velcro connector 102, further advantages of varying the size of the wrap to a particular foot may be gained, and adjustability of the rear straps allow selected positioning of the cushion 92 while also allowing further control of the restriction on motion of the sagittal plane of the heel. As noted above, any combination of flexible or non-flexible materials for panel 82 and straps 84, 86, 88 and 90 may be possible and conveniently employed while maintaining comfort to the wearer.

Although the present invention has been described with particularity relative to the foregoing detailed description of the preferred embodiment, various modifications, changes, additions and applications other than those specifically mentioned herein will be readily apparent to those having normal skill in the art without departing from the spirit and scope of this invention.

I claim:

1. A foot support apparatus for supporting the metatarsal arch of the foot, comprising:
   a flexible base support member adapted to be positioned in underlying relationship to the metatarsal arch of the foot forward of the heel;
   a first elongated strap adapted to extend around the heel of the foot and having opposite end portions attached to opposite sides of said base support member;
   a second elongated strap adapted to extend across the upper portion of the foot at the metatarsal regions, said second elongated strap having opposite end portions attached on opposite sides of said base support member to one of said base support member and said first elongated strap; and
   a flexible pad secured to said base support member and adapted to underlie said metatarsal arch, a portion of one of said base support member and said first elongated strap extending upwardly from said pad along opposite sides of the foot.

2. A foot support apparatus according to claim 1 wherein at least one of said first and second elongated straps is formed in two sections and including releasable attachment means for interconnecting said two sections.

3. A foot support apparatus according to claim 2 wherein said releasable attachment means includes a pair of Velcro attachment strips, said support member having a length longitudinally of the foot greater than the width of said second strap.

4. A foot support apparatus according to claim 1 or 2 wherein at least one of said first and second elongated straps is made of an elastic material.

5. A foot support apparatus according to claim 1 or 2 wherein said flexible base support member is a fabric panel constructed out of an elastic material.

6. A foot support apparatus according to claim 5 wherein at least one of said first and second elongated straps is constructed out of an elastic material.

7. A foot support according to claim 1 wherein said first elongated strap is adapted to extend around the heel of the foot generally in a direction parallel to the plane of the sole of the foot.

8. A foot support apparatus for supporting the metatarsal arch of a human foot, comprising:
   a flexible support panel;
   a first flexible strap attached at one end portion to said support panel entirely along one side thereof and at its opposite end portion to said support panel entirely along the side thereof opposite said one side so that said end portions of said first flexible strap extend generally vertically along opposite sides of the foot;
   a second flexible strap having a first end attached to said one end portion and having a free end;
   a third flexible strap having a first end attached to the oppostie end portion of said first flexible strap and having a free end;
   interconnecting means associated with the free ends of said second and third flexible straps for releasably connecting said free ends to one another; and
   flexible pad means for supporting the metatarsal arch of the foot forward of the heel secured to said support panel and said pad means adapted to be positioned beneath the metatarsal arch of the foot.

9. A foot support apparatus according to claim 8 wherein said first, second and third flexible straps are inelastic and said support panel is elastic.

10. A foot support apparatus according to claim 8 wherein said pad means being a cushion oval in shape and approximately 0.5 centimeters thick and constructed of a closed cell foam plastic material.

11. A foot support apparatus for supporting the metatarsal arch of a human foot, comprising:
   a flexible elastic support panel adapted to be positioned in underlying relationship to the metatarsal arch of the foot forward of the heel, said panel having a rear edge located adjacent the heel of the foot, a forward edge generally parallel to said rear edge and a pair of side edges;
   a first elongated inelastic strap having opposite end portions each attached along a common side edge of said first strap to a respective side edge of said panel, said first strap adapted for extending around the heel of the foot with said end portions extending upwardly along the sides of the foot, each of said side edges of said panel attached entirely along its length to its respective opposite end portion of said first strap;
   a second elongated strap attached at its opposite ends to the opposite end portions of said first strap and adapted to extend around the upper part of the foot forward of the ankle, said second strap having a width smaller than the length of said panel; and
   an arch support pad secured to said panel in a position underlying said metatarsal arch.

* * * * *

UNITED STATES PATENT AND TRADEMARK OFFICE
CERTIFICATE OF CORRECTION

PATENT NO. : 4,271,605

DATED : 9 June 1981

INVENTOR(S) : RACZKA, EDWARD

It is certified that error appears in the above—identified patent and that said Letters Patent is hereby corrected as shown below:

Column 6, line 8, "unlerlie" should read --underlie--.

Column 8, line 14, "oppostie" should read --opposite--.

Signed and Sealed this

Twenty-seventh Day of October 1981

[SEAL]

Attest:

GERALD J. MOSSINGHOFF

Attesting Officer     Commissioner of Patents and Trademarks